United States Patent [19]
Kamppeter

[11] Patent Number: 5,420,651
[45] Date of Patent: May 30, 1995

[54] REFRACTION DEVICE FOR THE SUBJECTIVE DETERMINATION OF THE SPHERICAL AND ASTIGMATIC SIGHT PROPERTIES OF THE EYE

[76] Inventor: Bernd Kamppeter, Laimbacher Strasse 69, 95447 Bayreuth, Germany

[21] Appl. No.: 244,693
[22] PCT Filed: Jan. 28, 1993
[86] PCT No.: PCT/DE93/00081
§ 371 Date: Jun. 6, 1994
§ 102(e) Date: Jun. 6, 1994
[87] PCT Pub. No.: WO93/14691
PCT Pub. Date: Aug. 5, 1993

[30] Foreign Application Priority Data
Feb. 1, 1992 [DE] Germany ............... 42 02 902.3

[51] Int. Cl.⁶ ............................................. A61B 3/02
[52] U.S. Cl. ................................. 351/222; 351/236
[58] Field of Search ............ 351/222, 227, 228, 233, 351/236, 241

[56] References Cited
U.S. PATENT DOCUMENTS

| | | | |
|---|---|---|---|
| 2,024,376 | 12/1935 | Lee | 351/236 |
| 3,240,548 | 3/1966 | Biessels | 351/222 |
| 3,811,756 | 5/1974 | Apple et al. | 351/222 |
| 3,822,932 | 7/1994 | Humphey | 351/222 |
| 3,927,933 | 12/1975 | Humphrey | 351/222 |
| 4,385,813 | 5/1983 | Klein et al. | 351/217 |
| 4,529,280 | 7/1985 | Nohda | 351/211 |
| 4,834,526 | 5/1989 | Kabayashi | 351/208 |
| 4,943,162 | 7/1990 | Sims | 351/235 |

FOREIGN PATENT DOCUMENTS
1155615 10/1963 Germany .

OTHER PUBLICATIONS
Article—Der neue Zeiss-Kreuzzylinder-Simultantest, dated Feb. 1967.

Primary Examiner—William L. Sikes
Assistant Examiner—Huy Mai
Attorney, Agent, or Firm—Bachman & LaPointe

[57] ABSTRACT

There is described a refraction device for the subjective determination of the spherical and astigmatic sight properties of the eye of a patient, which has a beam dividing device for two partial beam paths. Arranged in each partial beam path is a cylindrical compensator which has at least one positive cylindrical lens and at least one negative cylindrical lens. The or each positive and negative cylindrical lenses of each cylindrical compensator are displaceable relative to each other by means of a first drive device for cylinder height determination. Each cylindrical compensator is rotatable by means of a second drive device for cylinder axis determination. The sphere can be adjusted by means of a commercially available phoropter or by means of a disk having spherical lenses or by means of a range selector plate with spherical lenses or by focal point adjustment of converging lenses corresponding to the principle of the astronomical telescope.

19 Claims, 4 Drawing Sheets

REFRACTION DEVICE FOR THE SUBJECTIVE DETERMINATION OF THE SPHERICAL AND ASTIGMATIC SIGHT PROPERTIES OF THE EYE

BACKGROUND OF THE INVENTION

The invention concerns a refraction device for the subjective determination of the spherical and astigmatic sight properties of the eye having a device for beam division into two partial beam paths, whereby at least one sight character is divided in the eye into two comparative images which can be perceived with a look, and an optical device which is associated with the respective partial beam path and which is suitable for setting given optical properties in the two partial beam paths.

Such a refraction device is known from German published specification (DE-AS) No 1 155 615 or from the German journal 'Der Augenoptiker', issue 2, 1967, pages 7 to 10 and 39. In that known refraction device, the optical device used is cylindrical lenses with which the comparative images of the sight character can be made different only by ±0.25 diopters. If the eye to be examined has poor eyesight, those minor diopter differences however are scarcely perceptible. A further disadvantage with that known refraction device is that the cylinder axis determination operation involves comparing together lenses whose resulting cylinder axis are unknown to the person carrying out the examination, and whose astigmatic difference is only ±0.25 diopters even in the case of the highest cylinders. In addition that known refraction device has a rigid prismatic displacement for dividing a beam into two partial beam paths and is therefore only suitable for the so-called 5-meter viewing distance as an accessory device for a commercially available phoropter. That rigid prismatic displacement only permits an eye examination with a sight character of a visual acuity of 0.6. Smaller sight characters have the result that the comparative images are too far apart and larger sight characters result in overlapping of the comparative images. Both of those however are disadvantageous in terms of exact subjective comparison. A further disadvantage which is not to be underestimated with that known refraction device for simultaneous testing is that for the cylinder axis determination operation, it is necessary for the refraction device to be appropriately turned. As a result however the comparative images lose their association so that the communication between the patient and the person operating the refraction device is impaired or made more difficult. In addition, due to the asymmetrical beam path in that known refraction device one object or comparative image is produced a few centimeters nearer than the other object or comparative image. A further deficiency is that the examination strategy or procedure with that refraction device is just as difficult to learn as with the conventional refraction devices as it is not possible for a user to be guided by means of a computer.

U.S. Pat. No. 4,943,162 discloses a refraction device having a cylinder compensator which forms an accessory device for conventional phoropters. That refraction device is intended to enable a patient himself to adjust his astigmatic defect by the use of two successively arranged Sims lenses, that is to say cylindrical lenses which are arranged in succession. It is not possible with that known refraction device for two comparative images to be simultaneously compared to each other in order in that way to provide for subjective determination of the sight properties of the eye. That means however that the refraction determination operation which is carried out with that refraction device, without comparative images, is probably impossible for a proportion of the order of magnitude of 80% of the normal ophthalmologist public.

U.S. Pat. No. 4,529,280 discloses a near vision device which however is not capable of effecting simultaneous image comparison. It is not possible in that case to provide for determining visual acuity with variable sight characters. The step of ascertaining refraction is effected in accordance with an assessment on the part of the patient who however does not have comparative images simultaneously available. All experience in ophthalmology shows however that with a majority of patients that results in incorrect results. Ophthalmological examination methods are also described for example in the German book by W Straub, Volume II, Ferdinand-Enke-Verlag Stuttgart 1976.

U.S. Pat. No. 4,834,527 describes a device for safeguarding the distance between a patient and an ophthalmological device using the principle of the so-called Non-Contact-Tonometer.

SUMMARY OF THE INVENTION

The object of the present invention is to provide a refraction device of the kind discussed above, which is of a simple configuration and which is simple to operate and with which it is possible to achieve a substantial improvement in determining spectacles.

In a refraction device of the kind discussed above, in accordance with the invention that object is attained in that disposed in each of the partial beam paths as the optical device is a cylindrical compensator which has at least one positive cylindrical lens and at least one negative cylindrical lens, wherein the/each positive and negative cylindrical lens provided in the corresponding partial beam path are rotatable relative to each other by means of an associated first drive device about the corresponding partial beam path axis for cylinder height adjustment and wherein the/each positive and the/each negative cylindrical lens of each partial beam path are respectively jointly rotatable by means of an associated second drive device about the corresponding partial beam path axis for corresponding cylinder axis adjustment. If the positive cylindrical lens has for example +4 diopters and the negative cylindrical lens has −4 diopters, then all cylindrical values between +4 and −4 diopters can be simulated in each of the two partial beam paths. With a refraction device of such a design configuration it is possible to correct 8 diopters astigmatism. That diopter range covers more than 99% of all spectacles refractions. Likewise it is easily possible with the refraction device according to the invention for all cylinder axes between 0 and 180 degrees of angle to be directly and definedly produced in each of the two partial beam paths, and compared together. They may be adapted to the variable sight capabilities of the patients. Rotation of each of the two cylindrical compensators and rotation of the two cylindrical lenses of the corresponding cylindrical compensator is possible in accordance with the invention for example by means of stepping motors in each case for example through angular steps which can be 1 degree of angle. That means however that the spherical and astigmatic sight properties of the eye of a patient can be very accurately determined with the refraction device according to the invention. It is not possible to achieve a comparable degree of accuracy with manually operable cylindrical compensators.

BRIEF DESCRIPTION OF THE DRAWINGS

Further details, features and advantages will be apparent from the following description of embodiments of the refraction device according to the invention, which are diagrammatically illustrated in the drawings in which.

DETAILED DESCRIPTION OF THE PREFERRED EMBODIMENTS

As already mentioned, with the refraction device according to the invention the positive cylindrical lens may have for example +4 diopters and the negative cylindrical lens, of each of the two cylindrical compensators, may have −4 diopters, or more. In order to cover such a diopter range, in the case of the above-mentioned known refraction device in accordance with Biessels, as is described in above-mentioned DE-AS No 1 155 615, thirty two lenses are required due to the 0.25 diopter spacings. In comparison only two lenses are required in accordance with the invention. With a total of four lenses, in the case of cylindrical compensators, all four lenses can be directly compared to each other between 0 and 8 diopters steplessly in all axis positions. In the case of the above-mentioned device to Biessels, in spite of the use of thirty two lenses, only lenses with a 0.5 diopter difference and axis positions at 90° can be compared to each other.

In accordance with the invention the beam dividing device may have two pairs of mirrors which are respectively at least approximately parallel to each other and which diverge away from the patient side, the pairs of mirrors being at least approximately perpendicularly oriented relative to each other. Said pairs of mirrors may be replaced by suitable prisms.

In the case of a refraction device of the above-indicated kind the one pair of mirrors can be stationary and a mirror of the second pair of mirrors can be adjustable in respect of its angle relative to the other mirror of the second pair of mirrors by means of a third drive device for alignment of the two partial beam paths with a single sight character. Such a configuration of the refraction device according to the invention requires only a single sight character for simultaneous observation. By virtue of the possibility of being able to displace the associated mirror of the second pair of mirrors as desired by means of the above-mentioned third drive device, the refraction device according to the invention is advantageously equally suitable for sight characters of any size, because overlapping of the two simultaneously provided comparative images or excessively wide divergence thereof from each other are avoided by suitable adjustment of the inclination of the mirror connected to the third drive device.

With the refraction device according to the invention as an accessory for a conventional phoropter, for suitable sphere comparison there can be provided a plate or disk which is provided with spherical lenses and with a shutter and which is arranged on the side remote from the patient after the two cylindrical compensators and which is rotatable by means of a fourth drive device about an axis of rotation that is parallel to the two partial beam paths. Such a configuration of the refraction device, by means of the fourth drive device, makes it possible for example to close one of the two partial beam paths or to dispose different spherical lenses in both partial beam paths in order to produce spherically different comparison images.

Refraction devices of the above-described kind may have a mounting portion which is disposed on the side towards the patient and which forms a device entrance pupil, for fixing the refraction device in the form of a front accessory device on a par se known phoropter. Such a refraction device can therefore be combined with any commercially available phoropter in order in that way to ascertain all three parameters of subjective refraction, that is to say sphere, cylinder height or cylindricity and axis position of the cylinder, in a simultaneous comparison mode. Those three parameter values mutually influence each other, and such mutual influence can be dealt with more easily and in less time by means of the refraction device according to the invention, without adversely affecting the operation of determining said three parameter values. Considerably different lenses of equal spherical equivalents, for example −1.0 sph. with +/−0 −2.0/90° can be directly and simultaneously compared together, which was hitherto not possible with any method. Misunderstandings between the patient and the person carrying out the examination are avoided. In conventional examination there is a conflict of interest between the patient and the refractionist. The patient would like to have the maximum amount of time to view and decipher the sight characters which are established at the limit of vision. The doctor however must offer the comparative lenses in succession as quickly as possible so that the sight impression to be compared does not vanish from the short-term memory of the patient.

To provide an independent device in the form of a complete phoropter with simultaneous comparison for the 5-meter sight test distance, it is possible to dispose on the side of the refraction device according to the invention, that is towards the patient, two mutually parallel plates or disks with spherical lenses arranged in the common beam path in front of the device entrance pupil, wherein the spherical lenses of the one disk have a diopter interval or difference which is large in comparison with the diopter interval or difference of the spherical lenses of the second disk. The two disks are desirably rotatable by means of a fifth drive device. In that case the spherical lenses of the one disk may have for example an interval of three diopters from each other in each case and the spherical lenses of the second disk may respectively have an interval of 0.25 diopters. By means of those disks, when using for example eleven lenses with the 0.25 diopter interval and eleven lenses in the 3 diopter range, by addition, it is possible to produce all spherical lenses between +18.0 and −17.75 diopters. The different cylinder sizes and axes are produced by the prescribed cylindrical compensators in the respective beam path. The different spherical conditions are added, as in the case of the above-described front accessory device, by means of a disk on the side of the device which is remote from the patient. Operation is with a sight character device which reproduces the sight characters at the 5-meter distance.

Figure 3:
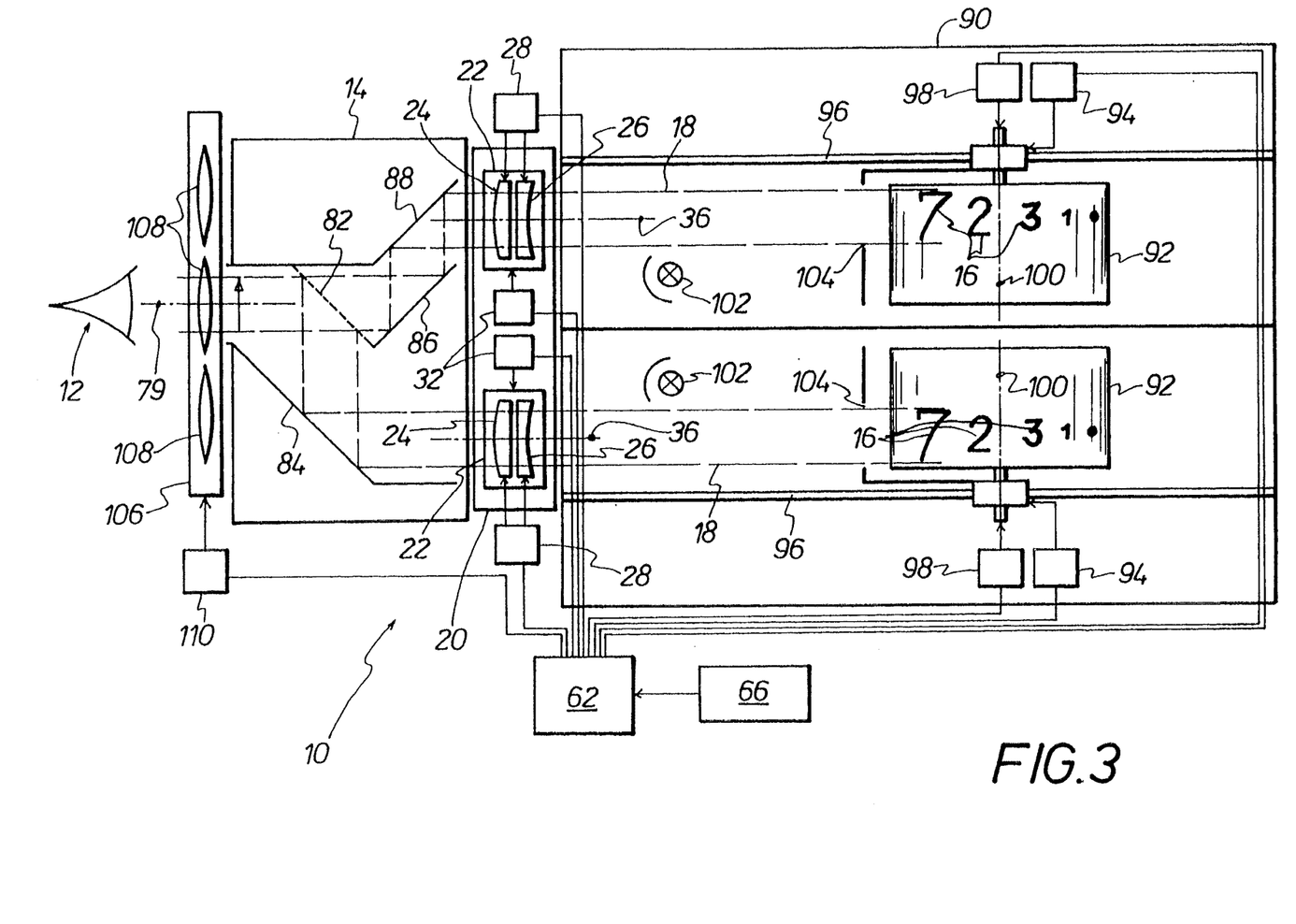
FIG. 3 shows a configuration of the refraction device for simultaneous refraction determination in the near range with two sight characters.

In accordance with the invention a further option is afforded by a device for simultaneous refraction determination in the near or close range. This refraction device can advantageously be of a small volume as it does not require a large amount of space or a 5-meter sight distance. With the specified refraction device according to the invention it is possible to myopise a patient at the entrance pupil of the device by a given amount, that is to say the far point of the patient can be displaced into the close proximity by putting positive lenses in front. For example the far point of a normally sighted person can be adjusted to 10 cm by putting +10 diopters in front. If a sight character is moved forwardly for example to 5 cm until the patient sees it as sharply focussed, that corresponds to a spherical refraction of the eye of the patient of −10 diopters. Conversely it must then be moved away for example from 10 cm to 20 cm until focussing occurs in order to correspond to a refraction of the eye of +5 diopters. If that range should not be adequate, due to a high level of myopia or hyperopia, suitable front-mount lenses in the disk 106 are selected. The following example may serve for further clarification:

A front-mount lens +/−0 with an interval of 5-20 cm covers the range of −20.0 to −5.0 spherical. The front-mount lens +20.0 sph. would for example cover the range of +/−0 sph. to +15.0 diopter with the same sight distance.

Another configuration of the refraction device according to the invention is characterized in that the beam dividing device has two successively arranged pairs of respectively parallel mirrors, wherein the one mirror of the one pair is a semi-transparent mirror behind which the first mirror of the second pair of mirrors is oriented at least approximately perpendicularly to the semi-transparent mirror of the first pair of mirrors and the second mirrors of the two pairs of mirrors are laterally displaced relative to each other. Such a refraction device can be intended for simultaneous refraction determination in the near region or for simultaneous refraction determination with sphere determination on the principle of the astronomical telescope. In the first-mentioned case, that is to say in the case of a refraction device for simultaneous refraction determination in the near region, there may be provided on the side of the beam dividing device that is remote from the patient, a sight character device with two sight character elements, each of which is arranged in an associated partial beam path and is linearly adjustable by means of an associated sixth drive device in relation to the beam dividing device. With such a refraction device it is desirable if in each partial beam path the corresponding cylindrical compensator which is connected to the first and second drive devices is arranged to be invariable in respect of position between the beam dividing device and the sight character device and if on the side towards the patient disposed in front of the beam dividing device is a range selector plate or disk with spherical lenses of different diopter numbers which can be selectively successively interchanged or arranged in the light beam of the entrance pupils by means of a seventh drive device and which can be disposed in front, for increasing range. With such a refraction device the patient can be myopised by a given amount by means of said range selector disk at the device entrance pupil. The differing spherical refraction is determined by appropriate linear displacement of the two sight character elements, that is to say by moving said sight character elements forwards or backwards. In the case of a myopic patient the sight character elements are moved closer while in the case of a hyperopic patient the sight character elements are moved correspondingly further away. The displacement distance corresponds to the spherical refraction of the patient. The measurement range of the refraction device can be adapted by said range selector plate or disk with the suitable positive lenses that are different from each other, to the measurement range of for example ±25 diopters and the sight character travel distance of for example 5 to 25 cm. Advantageously, when using a refraction device of such a configuration, instead of about 160 lenses in the case of refractions with a conventional testing assembly, in accordance with the invention only 4–6 lenses are required. The different spherical conditions in the two beam paths are produced by moving the sight character elements in different ways. The sight characters which are for example digits or letters are shown one above the other for example on two drums symmetrically in the two beam paths. The resulting image size differences in the eye due to the sight character elements coming closer are compensated by rotating the drums with sight characters decreasing in size.

A free-sight device, that is to say a device with fixed sight characters in the near range, for simultaneous refraction determination with sphere determination on the principle of the astronomical telescope, is achieved in the case of the refraction device according to the invention by virtue of the fact that in each partial beam path the corresponding cylindrical compensator which is connected to the first and second drive devices is disposed between two converging lenses and invariable in respect of position relative to same and in relation to the associated sight character element, in a corresponding telescope subsystem, wherein each of the two telescope sub-systems is adjustable by means of an associated eighth drive device linearly along the corresponding partial beam path relative to a converging lens which is stationarily arranged in the corresponding partial beam path on the side of the beam dividing device that is remote from the patient. In that respect, the configuration in the form of the free-sight device has the further quite considerable advantage that device accommodation is avoided. For that purpose, a semi-transparent mirror is desirably disposed in an inclined orientation on the side of the beam dividing device, that is towards the patient.

It has proven desirable if, in the refraction devices of the above-indicated kind, each of the two sight character devices has sight characters of different sizes and is adjustable by means of an associated ninth drive device relative to the corresponding partial beam path. Said sight characters may be letters and/or digits. As has already been mentioned, the sight character devices are desirably in the form of drums, on the peripheral surface of which the sight characters are disposed in such a way as to increase or decrease in size in a direction of rotation. In regard to subjective refraction, testing should be effected with the sight character which can still just be discerned as it is easier for the patient to distinguish two lenses as better or worse if with the one lens he can still discern the sight character but with the other lens he can no longer decipher it.

A refraction device which is simple to manage or simple to operate and which operates in accordance with the bracketing method according to the invention is provided if the two first and/or the two second and-/or the third and/or the fourth and/or the fifth and/or the two sixth and/or the seventh and/or the two eighth and/or the two ninth drive devices are stepping motors which are connected to a microcomputer. The appropriate displacements in angular steps of for example 1 degree of angle can thus be produced with a very high degree of accuracy by means of the above-mentioned stepping motors. Sphere and cylinder size of the lenses which are to be compared together can thus be produced in a virtually stepless fashion. In the case of poor vision a large sight character is selected and it is reduced until the limit of vision is reached. Then large spherical lenses are compared together and whenever an improvement in vision is produced by a lens, the sight character is reduced in size until the limit of vision is reached. Thereafter, spherical lenses are presented, which are at half the interval from the previously better lens. Thus, by questioning the patient, the true spherical refraction of the patient is attained in a plurality of steps, by a procedure whereby the optimum visual acuity of the patient is approached by bracketing of the lenses and adjustment of the sight character. That is achieved in the same manner in regard to cylinder and cylinder axis.

By virtue of the use of the microcomputer, subjective refraction determination which can be carried out with the refraction device according to the invention can be standardized and can be of such a nature that even unqualified operating personnel can effect exact subjective spectacles determination. A patient can possibly even determine his refraction himself, by operating on the computer two keys which are associated with an improvement in the upper or lower beam path. That means however that the refraction device according to the invention is equally well suitable for exact subjective refraction determination of a very wide range of patients, not only for first-world countries but also for second-world or third-world countries. The use of a microcomputer and the stepping motors which are connected together therewith as drive devices afford a refraction device with which the operator only has to ask the patient the same question about ten to twenty times, for example whether the upper or lower image is seen to be sharper. The corresponding answer is inputted into the microcomputer, for which purpose it is connected for example to a keyboard. The microprocessor then computes the corresponding subjective refraction, in which case the result achieved is substantially better than the refraction result achieved with conventional methods. It will be appreciated that, with the refraction device according to the invention, the conventional method with comparison of two lenses in succession is also possible, and the conventional cross-cylinder method can be used instead of the bracketing method according to the invention. This achieves even the aim that could not be attained earlier, of successively offering two lenses and not wasting any time in the lens-change operation: that is possible for example by a procedure whereby the two lenses are preset in the respective beam path and the comparison lenses are presented in succession without delay simply by switching light sources on and off.

Figure 1:
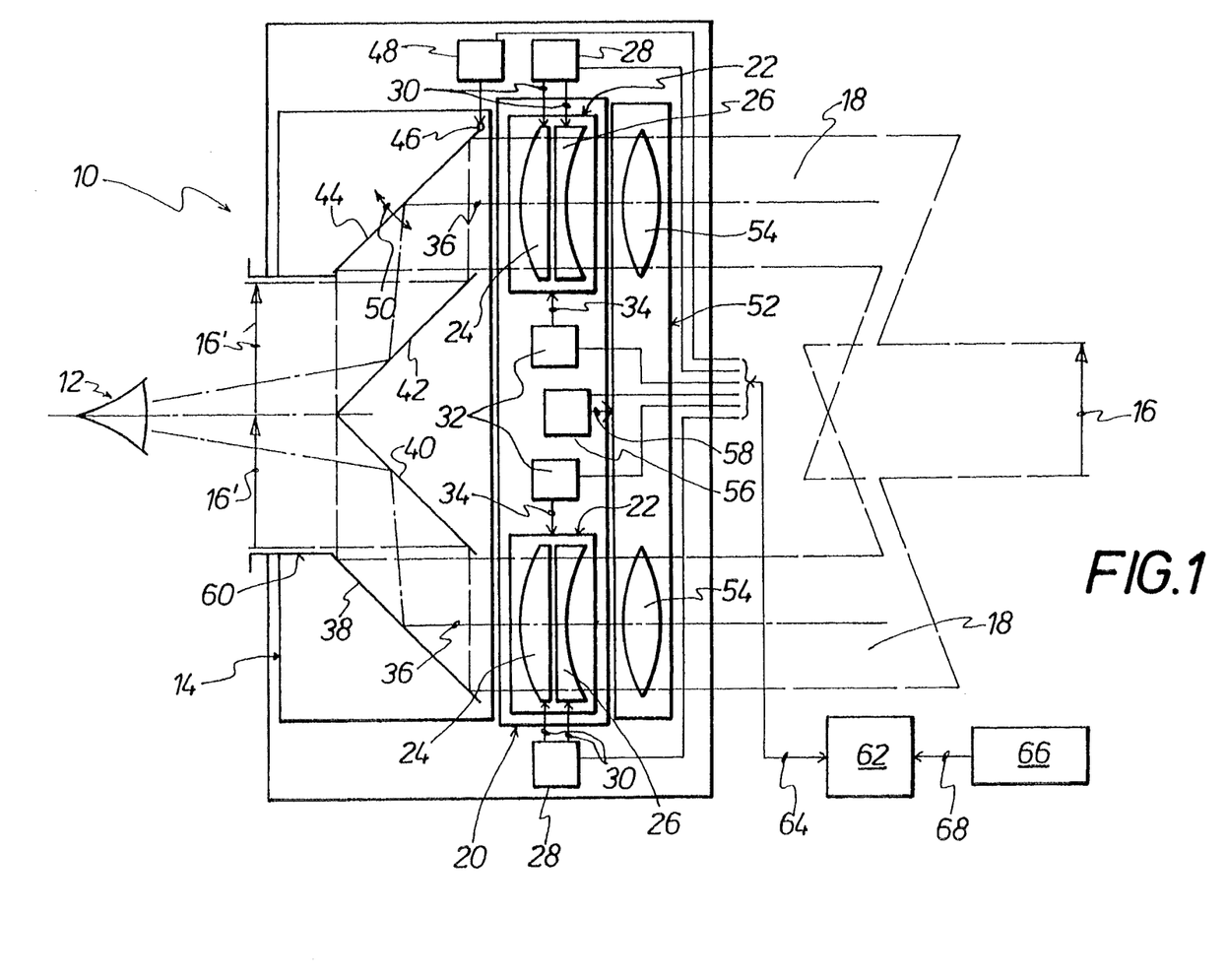
FIG. 1 shows a first embodiment of the refraction device which can serve as a front accessory device for a commercially available phoropter.

Referring to the drawings,

FIG. 1 diagrammatically shows a first configuration of the refraction device 10 for the subjective determination of the spherical and astigmatic sight properties of an eye 12 of a patient. The refraction device 10 has a beam dividing device 14 by which a single sight character 16 which may be for example a letter or a digit is divided into two partial beam paths 18. The sight character 16 is produced by a sight character projector at the 5 meter distance. Therefore the sight character 16 is divided in the eye 12 of the patient by the beam dividing device 14 into two sight characters 16' which can be simultaneously discerned with a look, that is to say which represent simultaneously discernible comparative images. Reference numeral 20 denotes by means of a block an optical device which is disposed on the side of the beam dividing device 14, that is remote from the patient 12, and which is associated with the two partial beam paths 18. The optical device 20 has two cylindrical compensators 22 which are disposed in the partial beam paths 18. Each of the two cylindrical compensators 20 has a positive cylindrical lens 24 and a negative cylindrical lens 26. The positive cylindrical lens 24 and the negative cylindrical lens 26 of each cylindrical compensator 22 is operatively connected to a first drive device 28, as is indicated by the arrows 30. By means of the first drive device 28 it is possible for the positive cylindrical lens 24 and the negative cylindrical lens 26 of the associated cylindrical compensator 22 to be rotated independently of each other relative to each other in order in that way to provide for a desired cylinder height adjustment. Each of the two cylindrical compensators 22 is also operatively connected to an associated second drive device 32, as is indicated by the arrows 34. By means of the second drive device 32 it is possible for the associated cylindrical compensator 22 to be rotated as a whole about the corresponding partial beam path axis 36 in order to provide for a desired cylinder axis adjustment.

The beam dividing device 14 has a first pair of mirrors 38 and 40 which are stationarily disposed in mutually parallel orientation. A second pair of mirrors 42 and 44 is disposed in mutually parallel relationship and oriented at least approximately perpendicularly or divergently relative to the first pair of mirrors 38, 40. The mirror 42 is arranged stationarily and the mirror 44 is pivotable relative to the mirror 42 about an axis of rotation 46 by means of a third drive device 48. That pivotability is indicated by the arcuate double-headed arrow 50.

Disposed on the side of the optical device 20, that is remote from the patient, is a plate or disk 52 which has spherical lenses 54 and a shutter so that suitable different spherical lenses 54 can be disposed in the two partial beam paths 18 or said shutter can be disposed in the one or other partial beam path 18. For that purpose the disk 52 is connected to a fourth drive device 56, as is indicated by the arrow 58.

On the side towards the patient the refraction device 10 is provided with a mounting portion 60 which forms a device entrance pupil. With that mounting portion 60 the refraction device 10 can be temporarily fixed as a front accessory device to a per se known phoropter.

The disk 52 with the spherical lenses 54 serves for producing a different sphere adjustment so that, by means of the above-mentioned disk 52 and by means of the optical device 20 and the use of the spherical lenses of the conventional phoropter (not shown) which is disposed in front, it is possible accurately to determine the three parameters of subjective refraction, sphere, cylinder height and cylinder axis position, preferably by means of a computer-controlled strategy or procedure. Accurate determination of said three parameters of subjective refraction is possible by virtue of the fact that the drive devices 28, 32, 48 and 56 are connected to a microcomputer 62, as is diagrammatically indicated by the double-headed arrow 64. A keyboard 66 is connected to the microcomputer 62, as is indicated by the arrow 68. Use of the microcomputer 62 with the keyboard 66 and the adjustability of the components by means of the drive devices 28, 32, 48 and 56 which are connected to the microcomputer afford the advantage that the person operating the refraction device 10 only has to ask the patient the same question about ten to twenty times, namely whether the upper or the lower image 16' is sharper. The corresponding answer is then entered into the microcomputer 62 by means of the keyboard 66. By suitable programming of the microcomputer 62 it is possible then to output therefrom without delay the correct parameters of sphere, cylinder height and cylinder axis position of the eye of the patient so that an optician can produce the appropriate spectacles.

Figure 2:
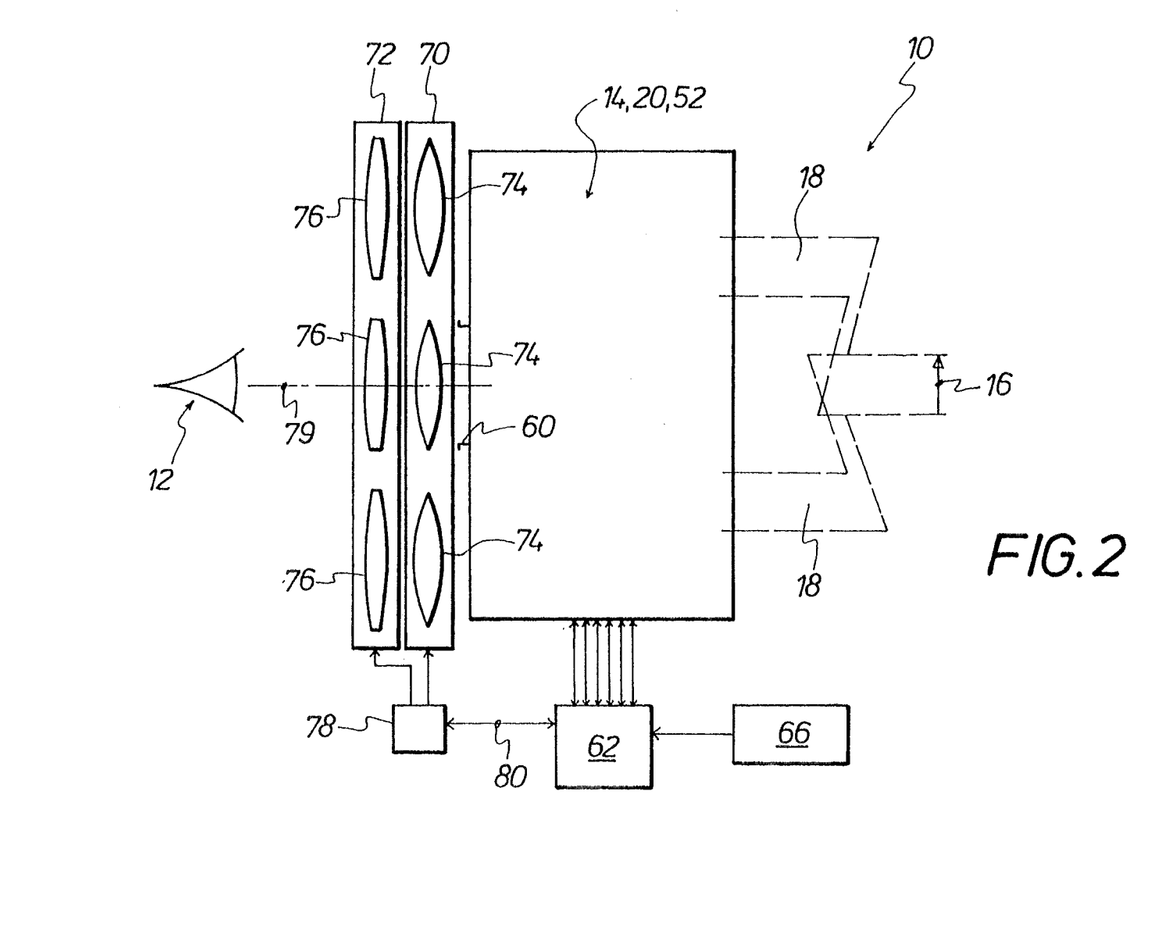
FIG. 2 diagrammatically shows a refraction device for the 5 meter sight distance which produces spherical refraction with two disks fitted with spherical lenses, the parts 14, 20, 52 of the device corresponding to those shown in FIG. 1.

FIG. 2 diagrammatically shows a configuration of the refraction device 10 for a single sight character 16, wherein the refraction device 10 is of a similar configuration to the refraction device 10 diagrammatically shown in FIG. 1 and all details thereof are not described here. The Figure only indicates the two divergent partial beam paths 18 on the side that is remote from the patient and the mounting portion 60, which is in the form of the device entrance pupil, on the side of the refraction device, that is towards the patient. Likewise FIG. 2 diagrammatically illustrates the microcomputer 62 and the keyboard 66 which is connected to the microcomputer 62. Disposed on the side of the device entrance pupil 60, that is towards the patient (eye 12), are two mutually parallel plates or disks 70 and 72 having spherical lenses 74 and 76 in order to constitute an independent device for the 5-meter vision distance. The spherical lenses 74 of the disk 70 have a diopter interval which is greater than that of the spherical lenses 76 of the second disk 72. For example the diopter interval of the spherical lenses 74 is three diopters while that of the spherical lenses 76 is only 0.25 diopter. The disks 70 and 72 are displaceable by a fifth drive device 78 in order suitably to arrange in the beam path 80 of the device exit pupil 60 a respective one of the spherical lenses 74 with one of the spherical lenses 76, that is to say to combine seine. The fifth drive device 78 which, as in the case of the drive devices 28, 32, 48 and 56 (see FIG. 1), is preferably an electrical stepping motor, is operatively connected to the microcomputer, as is indicated in FIG. 2 by the double-headed arrow 80.

FIG. 3 diagrammatically shows a configuration of the refraction device 10 for simultaneous refraction determination in the near range, having a beam dividing device 14 which is provided with two pairs, disposed one behind the other, of respectively parallel mirrors 82 and 84, and 86 and 88 respectively. The parallel mirrors 82 and 84 form the one pair of mirrors and the mirrors 86 and 88 form the second pair of mirrors. The mirror 82 is a semi-transparent mirror, behind which the first mirror 86 of the second pair of mirrors is disposed in at least approximately perpendicular orientation. The second mirrors 84 and 88 of the two pairs of mirrors are laterally displaced relative to each other. Such a configuration in respect of the beam dividing device 14 provides for division of the beech into two partial beam paths 18 for two sight characters 16. With this configuration of the refraction device 10 also, disposed in each of the two partial beam paths 18, on the side of the beam dividing device 14 that is remote from the patient (eye 12), is an optical device 20 with cylindrical compensators 22 which are each arranged in the associated partial beam path 18. Each of the two cylindrical compensators 22 has a positive cylindrical lens 24 and a negative cylindrical lens 26 which are rotatable relative to each other about the associated partial beam path axis 36 by means of a first drive device 28 in order to set a desired cylinder height. Each cylindrical compensator 22 is also connected to a second drive device 32 in order for the corresponding cylindrical compensator 22 to be rotated as a whole about the associated partial beam path axis 32. In that way it is possible to adjust the corresponding cylinder axis.

Disposed on the side of the beam dividing device 14 or the optical device 20, that is remote from the patient, is a sight character device 90 having two sight character elements 92. That makes it possible to provide for simultaneous refraction determination in the near range. Each of the two sight character elements is in the form of a drum which is linearly displaceable in relation to the optical device 20 along a guide device 96 by means of a sixth drive device 94. Each of the two sight character elements 92 which are in the form of drums has sight characters 16 of different sizes and is rotatable about its central axis 100 by means of a ninth drive device 98 in order as desired to move one of the sight characters 16 of different sizes into the corresponding partial beam path 18. That is effected in order to present the smallest possible sight character that can still be discerned, which is necessary for determining visual acuity and refraction, and also to compensate for the different sight character size in the eye, which is produced on the retina by the sight character carriage coming closer and moving away. Light sources 102 are provided for illuminating said sight characters 16. Each of the two partial beam paths 18 is directed by means of an aperture 104 accurately on to one of the sight characters 16 of the corresponding sight character element 92. The illumination serves for cutting out a beam path as desired. A further function is attributed thereto when using one of the conventional refraction strategies or procedures, when the lenses are successively presented by cutting the respective beam path in and out. A range selector plate or disk 106 with spherical lenses 108 with different diopter numbers can be provided in front of the beam dividing device 14, on the side that is towards the patient. The spherical lenses 108 can be arranged one after the other by means of a seventh drive device 110 in the light beam 79 of the entrance pupil. They serve to enlarge the measurement range in order to be able steplessly to present for example +20 dptr to −20 dptr.

The drive devices 28, 32, 94, 98 and 110 which are preferably: in the form of electrical stepping motors are connected to a microcomputer 62 which is combined with a keyboard 66. The mode of operation of the computer 62 with the keyboard 66 has already been described hereinbefore with reference to FIG. 1.

Figure 4:
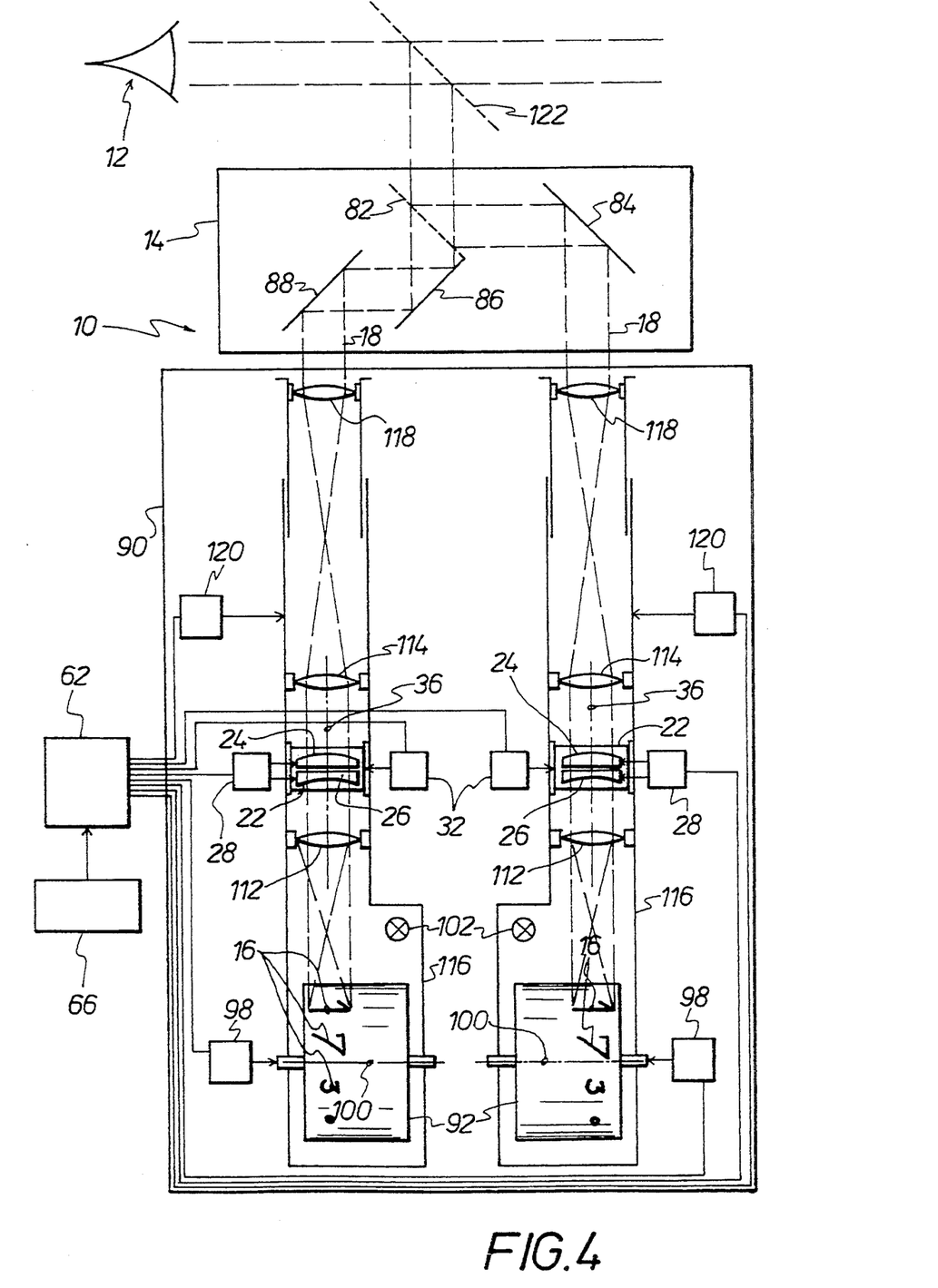
FIG. 4 shows a configuration of the refraction device as a free-sight device for simultaneous refraction determination with sphere determination on the principle of the astronomical telescope, with two sight characters.

FIG. 4 diagrammatically shows a refraction device 10 which is in the form of a free-sight device for simultaneous refraction determination with sphere determination on the principle of the astronomical telescope. It has a beam dividing device 14 with two pairs, arranged one behind the other, of respectively parallel mirrors 82, 84 and 86, 88, wherein the mirror 82 of the one pair of mirrors is in the form of a semi-transparent mirror as in the case of the beam dividing device 14 shown in FIG. 3. That in turn provides for beam division into two partial beam paths 18, a sight character 16 of a sight character element 92 being arranged in each partial beam path 18. Disposed in each partial beam path 18 is a cylindrical compensator 22 having a positive cylindrical lens 24 and a negative cylindrical lens 26. The positive and negative cylindrical lenses 24, 26 of each cylindrical compensator 22 are connected to a first drive device 28, by means of which it is possible for the positive cylindrical lens 24 and the negative cylindrical lens 26 to be rotated as desired relative to each other about the common partial beam path axis 36. In that way it is possible to set any desired cylinder height. Each cylindrical compensator 22 is also connected to an associated second drive device 32. By means of the second drive device 32 it is possible for the associated cylindrical compensator 22 to be rotated as a whole about the corresponding partial beam path axis 36 in order to determine the cylinder axis. Each of the two cylindrical compensators 22 is stationarily disposed between two converging lenses 112 and 114. The lens system 114, 24, 26 and 112 of each of the two partial beam paths 18 is also arranged stationarily relative to the associated sight character element 92. By virtue of that arrangement, associated with each of the two partial beam paths 18 is a telescope subsystem 116 which, in relation to a converging lens 118 stationarily arranged in the corresponding partial beam path 18, is linearly displaceable along said partial beam path 18 by means of an associated eighth drive device 120 in order to adjust sphere. The cylindrical compensators may also be introduced into the beam path between the lens 118 and the beam divider 14. The telescope system could also be replaced by movement of the lens 114 in the direction of the beam path.

Each of the two sight character elements 92 which are in the form of drums, with the sight characters 16 of different sizes, is connected to a ninth drive device 98, by means of which it is possible for the associated sight character element 92 to be rotated as desired about its central axis 100. This embodiment of the refraction device 10 also has light sources 102 to illuminate the sight characters 16 in the sight character arrangement 90.

The drive devices 28, 32, 98 and 120 which are preferably in the form of stepping motors are connected together to a microcomputer 62 connected to a keyboard 66. The mode of operation of the last-mentioned components has already been described hereinbefore so that there is no need for it to be described in detail once again.

A semi-transparent mirror 122 is provided on the side, that is towards the patient (eye 12), of the beam dividing device 14 of the refraction device 10 shown in FIG. 4, to constitute a free-sight device.

I claim:

1. A refraction device for the subjective determination of the spherical and astigmatic sight properties of the eye of a patient, which comprises: a device for dividing a beam into two partial beam paths whereby said device forms two comparative images of at least one sight character in the eye which can be perceived with a look; an optical device which is associated with the respective partial beam path and which is provided for setting given optical properties in the two partial beam paths; wherein disposed in each of the two partial beam paths as the optical device is a cylindrical compensator which has at least one positive cylindrical lens and at least one negative cylindrical lens; and wherein said each positive and negative cylindrical lens provided in the corresponding partial beam path are rotatable relative to each other by means of a first drive device about the corresponding partial beam path axis for cylinder height adjustment; and wherein said each positive and said each negative cylindrical lens of each cylindrical compensator are respectively jointly rotatable by means of a second drive device about the corresponding partial beam axis for corresponding cylinder axis adjustment.

2. A refraction device as set forth in claim 1, wherein the beam dividing device has two pairs of mirrors which are respectively at least approximately parallel to each other and which diverge away from the patient's side, the pairs of mirrors being at least approximately perpendicularly oriented relative to each other.

3. A refraction device as set forth in claim 2, wherein one pair of mirrors is stationary and a mirror of the second pair of mirrors is adjustable in respect of its angle relative to the other mirror of the second pair of mirrors by means of a third drive device for alignment of the two partial beam paths with a single sight character.

4. A refraction device as set forth in claim 3 wherein said third drive device is a stepping motor connected to a microcomputer.

5. A refraction device as set forth in claim 1, wherein for spherical comparison there is provided a disk which is provided with spherical lenses and which is arranged on the side remote from the patient after the cylindrical compensators and which is rotatable by means of a fourth drive device about an axis of rotation that is parallel to the two partial beam paths.

6. A refraction device as set forth in claim 5 wherein said fourth drive device is a stepping motor connected to a microcomputer.

7. A refraction device as set forth in claim 1, including a mounting portion which is disposed on the side towards the patient and which forms a device entrance pupil, for fixing the refraction device, in the form of a front accessory device on a phoropter.

8. A refraction device as set forth in claim 7, wherein disposed on the side of the device entrance pupil that is towards the patient, for forming a device for a 5-meter sight distance, are two mutually parallel disks with spherical lenses which can be arranged in the common beam path in front of the device entrance pupil, wherein the spherical lenses of one disk having a diopter interval which is large in comparison with that of the spherical lenses of the second disk, and the two disks are rotatable as desired by means of a fifth drive device.

9. A refraction device as set forth in claim 8, wherein the beam dividing device has two successively arranged pairs of respectively parallel mirrors, wherein one mirror of one pair of mirrors is a semi-transparent mirror, behind which the first mirror of the second pair of mirrors is oriented at least approximately perpendicularly to the semi-transparent mirror of the first pair of mirrors, and the second mirrors of the two pairs of mirrors are laterally displaced relative to each other.

10. A refraction device as set forth in claim 9, wherein disposed on the side of the beam dividing device that is remote from the patient for simultaneous refraction determination in the near region is a sight character device with two sight character elements, each of which is arranged in a partial beam path and is linearly displaceable by means of a sixth drive device in relation to the beam dividing device.

11. A refraction device as set forth in claim 10 wherein each of the two sight character elements has sight characters of different sizes and is adjustable by means of a ninth drive device relative to the corresponding partial beam path.

12. A refraction device as set forth in claim 11 wherein at least one of the sixth and ninth drive devices are stepping motor connected to a microcomputer.

13. A refraction device as set forth in claim 9, wherein in each partial beam path the corresponding cylindrical compensator which is connected to the first and second drive devices is arranged to be invariable in respect of position between the beam dividing device and the sight character device, and on the side towards the patient in front of the beam dividing device is a range selector disk with spherical lenses of different diopter numbers which can be selectively successively interchanged and arranged in the light beam of the entrance pupil by means of a seventh drive device.

14. A refraction device as set forth in claim 13 wherein the seventh drive device is a stepping motor connected to a microcomputer.

15. A refraction device as set forth in claim 9, wherein in each partial beam path the cylindrical compensator which is connected to the first and second drive devices is disposed between two converging lenses invariably in respect of position relative to same and in relation to the sight character element, in a corresponding telescope sub-system, and wherein each of the two telescope sub-systems is adjustable by means of an eighth drive device linearly along the corresponding partial beam path relative to a converging lens which is stationarily arranged in the corresponding partial beam path on the side of the beam dividing device that is remote from the patient.

16. A refraction device as set forth in claim 15, including a semi-transparent mirror which is disposed in an inclined orientation on the side of the beam dividing device that is towards the patient to provide a free-sight device.

17. A refraction device as set forth in claim 15 wherein the eighth drive device is a stepping motor connected to a microcomputer.

18. A refraction device as set forth in claim 8 wherein said fifth drive device is a stepping motor connected to a microcomputer.

19. A refraction device as set forth in claim 1 wherein at least one of said first drive device and said second drive device are stepping motors connected to a microcomputer.

* * * * *